United States Patent
Washburn et al.

(10) Patent No.: US 11,806,370 B2
(45) Date of Patent: Nov. 7, 2023

(54) METHODS OF PREPARING AND USING PLACENTAL TISSUE COMPOSITIONS

(71) Applicant: Plakous Therapeutics, Inc., Winston-Salem, NC (US)

(72) Inventors: Scott A. Washburn, Pfafftown, NC (US); Seth Tomblyn, Winston-Salem, NC (US)

(73) Assignee: Plakous Therapeutics, Inc., Winston-Salem, NC (US)

( * ) Notice: Subject to any disclaimer, the term of this patent is extended or adjusted under 35 U.S.C. 154(b) by 126 days.

(21) Appl. No.: 17/214,144

(22) Filed: Mar. 26, 2021

(65) Prior Publication Data

US 2021/0213070 A1 Jul. 15, 2021

Related U.S. Application Data

(62) Division of application No. 16/480,395, filed as application No. PCT/US2018/016383 on Feb. 1, 2018, now Pat. No. 10,960,028.

(60) Provisional application No. 62/453,335, filed on Feb. 1, 2017.

(51) Int. Cl.
*A61K 35/50* (2015.01)
*A61P 17/02* (2006.01)
*A61K 9/70* (2006.01)

(52) U.S. Cl.
CPC ............ *A61K 35/50* (2013.01); *A61K 9/7007* (2013.01); *A61P 17/02* (2018.01)

(58) Field of Classification Search
CPC ...................................................... A61K 35/50
See application file for complete search history.

(56) References Cited

U.S. PATENT DOCUMENTS

| | | | |
|---|---|---|---|
| 10,960,028 B2 | 3/2021 | Washburn et al. | |
| 2003/0235580 A1 | 12/2003 | Zhang | |
| 2007/0071740 A1 | 3/2007 | Tseng et al. | |
| 2011/0206776 A1 | 8/2011 | Tom et al. | |
| 2013/0245528 A1* | 9/2013 | Harrell | A61L 27/54 602/50 |
| 2015/0010609 A1 | 1/2015 | Tom et al. | |
| 2015/0367020 A1 | 12/2015 | Andrews et al. | |

FOREIGN PATENT DOCUMENTS

| | | |
|---|---|---|
| CN | 102327640 | 1/2012 |
| CN | 103114073 | 5/2013 |
| CN | 103861151 | 6/2014 |
| CN | 103520780 | 3/2015 |
| JP | 2014098021 | 5/2014 |
| WO | 2008/060377 | 5/2008 |
| WO | 2013/082158 | 6/2013 |
| WO | 2015/038477 | 3/2015 |

(Continued)

OTHER PUBLICATIONS

English machine translation of Xu et al., CN 103861151 A, 2014.*

(Continued)

*Primary Examiner* — Rosanne Kosson
(74) *Attorney, Agent, or Firm* — Kilpatrick Townsend & Stockton LLP

(57) ABSTRACT

Methods of preparing placental tissue products/compositions are disclosed together with methods of utilizing the placental tissue composition for delivery of a therapeutic agent.

14 Claims, 8 Drawing Sheets

(56) References Cited

FOREIGN PATENT DOCUMENTS

| WO | 2015/171142 | 11/2015 |
| --- | --- | --- |
| WO | 2017/160804 | 9/2017 |

OTHER PUBLICATIONS

Schweizer, Amniotic Membrane of the Placenta—Part 1, Parent's Guide to Cord Blood Foundation, https://parentsguidecordblood.org/en/news/amniotic-membrane-placenta-part-1, 2016.*
Protease/Phosphatase Inhibitor Cocktail (100X), Cell Signaling Technology, Inc., Available online at: https://media.cellsignal.com/pdf/5872.pdf, Jan. 1, 2014, 1 page.
Janson, J., "Protein Purification: Principles, High Resolution Methods, and Applications", 3rd Edition, Protein Purification, Mar. 2011, 12 pages.
Kim, J. et al., "Amniotic Membrane Patching Promotes Healing and Inhibits Proteinase Activity on Wound Healing Following Acute Corneal Alkali Burn", Experimental Eye Research., 70(3):329-337 (2000).
CA 3,016,606, "Office Action", dated Jul. 15, 2019, 3 pages.
CA 3,016,606, Office Action, dated Sep. 10, 2020, 4 pages.
CN 201780023893.3, Office Action, dated Jul. 10, 2020, 19 pages.
EP 17767314.2, "Extended European Search Report", dated Oct. 8, 2019, 7 pages.
EP 17767314.2, Office Action, dated Aug. 17, 2020, 5 pages.
PCT/US2017/022257, "International Preliminary Report on Patentability", dated Sep. 27, 2018, 6 pages.
PCT/US2017/022257, "International Search Report and Written Opinion", dated Jun. 8, 2017, 8 pages.
PCT/US2018/016383, "International Preliminary Report on Patentability", dated Aug. 15, 2019, 8 pages.
PCT/US2018/016383 , "International Search Report and Written Opinion", dated May 17, 2018, 12 pages.
"COmplete, Mini", Cat. No. 4693124, Roche, 2005, pp. 1-3.
"COmplete, Mini Protease Inhibitor Cocktail Tablets Provided in EASYpack", Roche, Product Information Sheet for 04693124001, Available Online at: https://www.sigmaaldrich.com/SG/en/product/roche/04693124001, 2002, 8 pages.
"Protease Inhibitor Cocktail for Use with Mammalian Cell and Tissue Extracts", Product Information Sheet for P8340, Available Online at URL: https://www.sigmaaldrich.com/SG/en/product/sigma/p8340, 2022, 1 page.
"Protease Phosphatase Inhibitor Cocktail (100X)", Cellsignal.com, Available Online at: https://media.cellsignal.com/pdf/5872.pdf, Jan. 1, 2014, 1 page.
"Report on the 18th Meeting of the Japan Society of Clinical Placenta Medicine < No. 1 > on the Difference Between Laennec and Melsmon and Mechanism of Action of Placenta", Skin Solution Clinics, 2015, pp. 1-4.
"Tissue", Merriam-Webster, Available Online at: https://www.merriam-webster.com/dictionary/tissue#:-text=Definition%20of%20tissue,a%20plant%20or%20an%20animal, 2022, 6 pages.
Ahmed, I. et al., "Processing of Procorticotropin-Releasing Hormone (Pro-CRH): Molecular Forms of CRH in Normal and Preeclamptic Pregnancy," J. Clin. Endocrinol. Metab. 85(2):755-764 (2000).
Kawakatsu, M. et al., "Placental Extract Protects Bone Marrow-Derived Stem/Progenitor Cells Against Radiation Injury Through Anti-Inflammatory Activity," J. Radiation Res., 54(2):268-276 (2013).
Kim, J. et al., "Protective Effects Of Human Placenta Extract On Cartilage Degradation In Experimental Osteoarthritis," Biol. Pharm. Bull., 33(6):1004-1010 (2010).
Kong, M. and Park, S., "Effect Of Human Placental Extract On Health Status In Elderly Koreans," Evidence-Based Complementary and Alternative Medicine, vol. 2012 (2012) (5 pages).
Naruse, K. et al., "Cytokines, Proteases, and Ligands of Receptor for Advanced Glycation Endproducts (Rage) Released by Primary Trophoblasts from Human Term Placenta Under Hypoxic Stimulation," Hypertens. Res. Pregnancy 1(2):81-87 (2013).
Shimoya et al., "Production of Leukocyte Chemotactic Factors (Interleukin-8 (IL-8)) and Monocyte Chemotactic Activating Factor (MCAF)) From Human Placental Chorionic Cells During Intra-Uterine Infection," Acta Obstetrica et Gynaecologica Japonica 45:S352 (1949) one page.
Varney, H. et al., "Varney's Midwifery," Jones and Bartlett Publishers, 2004, pp. 564-569.
Wilshaw, S. et al., "Biocompatibility and Potential of Acellular Human Amniotic Membrane to Support the Attachment and Proliferation of Allogeneic Cells," Tissue Engineering Part A 14(4):463-472 (2008).
Yoshida et al., "A Placenta Therapy and Integrated Medicine", Japanese placenta Tokyo Metropolitan Institute of Medical Science, No. 2, 2008, pp. 30-45.
U.S. Appl. No. 16/321,075, Non-Final Office Action, dated Feb. 2, 2022, 18 pages.
U.S. Appl. No. 16/321,075, Final Office Action, dated Sep. 16, 2022, 12 pages.
U.S. Appl. No. 16/480,395, Non-Final Office Action, dated Aug. 18, 2020, 8 pages.
U.S. Appl. No. 16/480,395, Notice of Allowance, dated Dec. 2, 2020, 10 pages.
AU 2017235220, First Examination Report, dated Oct. 30, 2021, 4 pages.
AU 2017235220, Notice of Acceptance, dated Mar. 9, 2022, 3 pages.
CA 3,016,606, Office Action, dated Oct. 15, 2021, 5 pages.
CN 201780023893.3, Notice of Decision to Grant, dated Nov. 8, 2021, 2 pages.
CN 201780023893.3, Office Action, dated Apr. 21, 2021, 9 pages.
EP 17767314.2, Notice of Decision to Grant, dated Nov. 25, 2021, 2 pages.
EP 21198147.7, Extended European Search Report, dated Apr. 26, 2022, 12 pages.
IN 201817034213, First Examination Report, dated Jun. 7, 2022, 8 pages.
JP 2018-549193, Office Action, dated Apr. 22, 2021, 6 pages.
JP 2018-549193, Notice of Decision to Grant, dated Mar. 1, 2022, 4 pages.
"Protease/Phosphatase Inhibitor Cocktail (100X). For Research Use Only. Not For Use in Diagnostic Procedures", Cellsignal Com, Available online at https://media.cellsignal.com/pdf/8872.pdf, 2014—1 page.
U.S. Appl. No. 16/321,075, "Non-Final Office Action", dated Aug. 24, 2023, 13 pages.
AU2022204044, "First Examination Report", dated Aug. 7, 2023, 4 pages.
Mihee et al. "Effect of Human Placental Extract on Health Status in Elderly Koreans", Evidence-Based Complementary and Affirmative Medicine, vol. 2012, 2012, pp. 1-5.
Powers et al., "Irreversible Inhibitors of Serine, Crystein, and Threonine Proteases", Chemical Reviews, vol. 102, No. 12, Nov. 8, 2022, pp. 4639-4750.

* cited by examiner

Amniotic Fluid

| | | |
|---|---|---|
| Amnion | Epithelium Layer | |
| | Basement Membrane | Collagen types III, IV, V; laminin, fibronectin, nidogen |
| | Compact Layer | Collagen types I, III, V, VI; fibronectin, |
| | Fibroblast Layer | Collagen types I, III, VI; laminin, fibronectin nidogen |
| | Intermediate (spongy) Layer | Collagen types I, III, IV; proteoglycans |
| Chorion | Recticular Layer | Collagen types I, III, IV, V, VI; proteoglycans |
| | Basement Membrane | Collagen types IV; fibronectin, laminin |
| | Trophoblasts | |

Maternal decidua

FIG. 1

METHODS OF PREPARING AND USING PLACENTAL TISSUE COMPOSITIONS

CROSS-REFERENCE TO RELATED APPLICATIONS

This application is a divisional of U.S. patent application Ser. No. 16/480,395, filed on Jul. 7, 2019, which is a U.S. national phase of International Application No. PCT/US2018/016383, filed on Feb. 1, 2018, which claims priority to and benefit of U.S. Provisional Patent Application No. 62/453,335, filed on Feb. 1, 2017, the entire contents of each of which is incorporated herein it its entirety for all purposes.

FIELD

Disclosed herein are biological compositions, methods of making compositions, and methods of using compositions. In embodiments, a composition is derived from placental membrane tissue.

BACKGROUND

The human placenta connects the fetus to the mother's uterine wall and is responsible for the protection and development of the fetus effectively from conception to the time of birth.

SUMMARY

The present invention relates to therapeutic compositions comprising placental tissue and associated methods of preparing and using placental tissue products/compositions. Placental tissue includes the placental disc and the amniotic sac. The amniotic sac comprises two primary layers, the chorion and the amnion. In an embodiment, a composition of the present invention comprises ex-vivo placental tissue treated with hydrogen peroxide ($H_2O_2$). In another embodiment, a composition comprises ex-vivo placental tissue treated with peracetic acid ($C_2H_4O_3$). In some embodiments, a composition may comprise an ex-vivo amnion treated with a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof. In some embodiments, a composition may comprise an ex-vivo amnion treated with a processing agent, wherein the processed amnion comprises an altered capacity to bind and/or release a pharmaceutical or therapeutic agent. In embodiments, the placental tissue comprises amnion. An amnion as described herein may comprise an amniotic membrane in its entirety or a portion thereof. In embodiments the composition may further comprise a therapeutic agent.

In certain embodiments, an amniotic membrane is processed to enhance its function as a delivery device for therapeutic agents including small molecules, proteins, cytokines, growth factors, cells, acellular placental products, and/or gene therapy agents. In an embodiment of the present invention, a method comprising processing an amnion in hydrogen peroxide to enhance the loading capacity of the amnion is provided. In an embodiment, the present invention provides a method comprising processing an amnion in peracetic acid to enhance the loading capacity of the amnion. In an embodiment, an amnion is loaded with therapeutic agents comprising small molecules, proteins, cytokines, growth factors, cells, gene therapy agents, and/or other therapeutic agents. In some embodiments, a method for enhancing a loading capacity of an amnion may comprise contacting an amnion with a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof.

In certain embodiments, compositions described herein may be used as a wound covering. In some embodiments, compositions may be used for local drug delivery. In some embodiments, the compositions may be used to aid in healing of burns, internal and external ulcers, surgical sites, nerve injuries, or other lesions. In certain embodiments, a method for treating a condition with an amnion may comprise loading a processed amnion with a therapeutic agent, wherein the therapeutic agent comprises any one of small molecules, proteins, cytokines, growth factors, gene therapy agents, cells, and combinations thereof, and placing the loaded amnion at a treatment location of a patient.

BRIEF DESCRIPTION OF THE DRAWINGS

FIG. 1 is a drawing depicting the layers of the placenta.

DETAILED DESCRIPTION OF THE INVENTION

Figure 2:
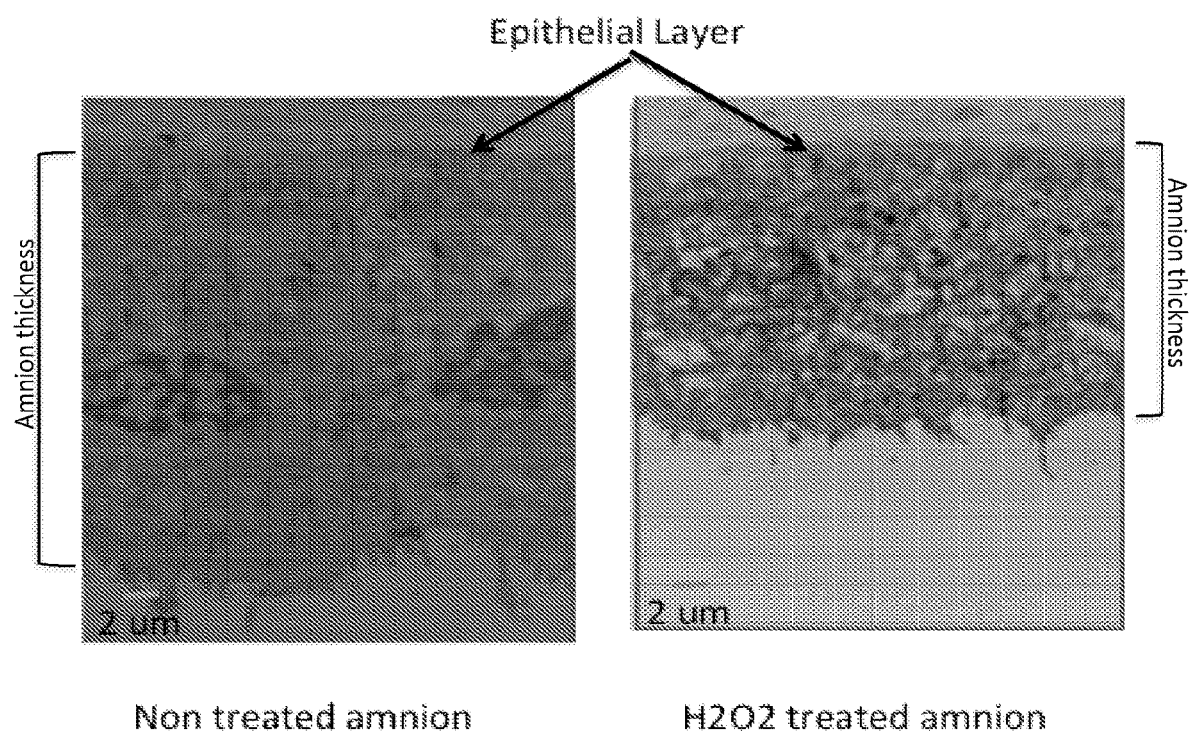
FIG. 2 is a micrograph of an amnion processed in hydrogen peroxide.

The present invention relates to compositions comprising placental tissue and associated methods of preparing placental tissue products/compositions. The human placenta connects the fetus to the mother's uterine wall and is responsible for the protection and development of the fetus effectively from conception to the time of birth. During pregnancy, the placenta helps the fetus develop by providing nutrients and oxygen, by performing some immunity functions, and by releasing growth factors and cytokines, small proteins that act to direct cell migration.

During pregnancy, the placenta provides nutrients, growth factors, and cytokines to the fetus via the umbilical cord and amniotic fluid. Both the fetus and placenta express antigens that are disparate from the mother, yet avoid being rejected by the maternal immune system during the pregnancy. The residual cells, transport properties, and limited immune response of placental tissue help make it desirable and/or advantageous to utilize placental tissue in medical applications.

Placental tissue may be typically collected after an elective Cesarean surgery. Placental tissue may also be collected after a normal vaginal delivery. The tissue may be used unmodified in some applications. However, it would be advantageous to improve the performance of placental tissue for enhanced medical applications. For example, it is advantageous and/or desirable to utilize placental tissue to deliver therapeutic agents for wound healing, osteoarthritis, pain management and the like.

For purposes of describing certain embodiments of the present invention, reference is made herein to human placenta tissue. Embodiments of the present invention, however, are not limited to comprising naturally occurring human placenta tissue. Embodiments of the present invention may include, but are not limited to: natural or synthetic human placenta tissue; natural or synthetic mammalian placenta tissue; natural or synthetic placenta tissue from other animals, e.g., bovine, equine, porcine, ovis, capra, or camelid; and/or natural and/or synthetic compositions having similar properties to placenta tissue. The placenta tissue described herein comprises ex-vivo tissue, where ex-vivo relates to use and treatment of the tissue outside the body of an organism.

Placenta tissue comprises the placental disc, the amniotic sac, the umbilical cord, its vessels, and Wharton's Jelly cushioning the umbilical cord vessels. The amniotic sac comprises the outer chorion and the inner amnion. The chorion and amnion are separable membrane layers.

The innermost layer of the placental tissues comprises the amnion. This membrane covers the embryo when it first forms, then fills with amniotic fluid to protect the fetus during development. The amniotic fluid transmits the placental-produced cytokines that orchestrate fetal growth and development from a single cell into a viable human. The amnion comprises a shiny, tough, avascular tissue comprised of several layers of connective tissue and a single layer of non-ciliated cells as shown in FIG. 1. Histological evaluation indicates that the amnion comprises a layered membrane comprising an epithelial cellular layer, a thin reticular fibrous layer (basement membrane), a thick compact layer, a fibroblast layer, and an intermediate spongy layer. The connective tissue layers of the amnion contain various collagens and proteins including collagen types I, III, IV, V, VI, as well as fibronectin, nidogen, laminin, and proteoglycans.

The maternal side of the amniotic sac comprises the chorion. The chorion may be three to four times thicker than the amnion and substantially cover the amnion. As shown in FIG. 1, the chorion comprises a reticular layer, basement layer, and trophoblast layer. The trophoblast layer may be adhered to the maternal decidua.

In vivo, the amnion may deliver between 200 and 500 mL of fluid per day between the placenta and amniotic fluid. Transfer of placental derived cytokines and fluid across the amniotic membrane may occur primarily via intramembranous transport either by diffusion through highly arborized tight junctions between amniocytes or by trans-cellular vesicle transport, which has been shown to be bi-directional. Thus, every layer of the amnion may comprise suffused cytokines and fluid. The amnion may function as a reservoir and delivery device for the cytokines synthesized and stored by cyto- and syncytiotrophoblasts and Hofbauer cells in the chorion.

Both the fetus and placenta may express antigens that are disparate from the mother, yet avoid being rejected by the maternal immune system during the pregnancy. The limited immuno response of the placental tissue is believed to assist the placenta in avoiding fetal rejection during pregnancy.

The transport properties, residual cells, and limited immune response of placental tissue help make it desirable to utilize placental tissue in medical applications. Placental tissue may be collected after an elective Cesarean surgery. Placental tissue may also be collected after a normal vaginal delivery. Placental tissue may be obtained through FDA registered tissue banks. The tissue may be used unmodified in some applications. However, it would be advantageous to improve the performance of the placental tissue for enhanced medical applications.

In embodiments, the present invention relates to placental tissue products and compositions. In some embodiments, a composition may comprise an amnion and a processing agent. In some embodiments, the processing agent may comprise an oxidizing agent. In some embodiments, the oxidizing agent may comprise hydrogen peroxide and/or peracetic acid. In some embodiments, a composition may comprise an amnion and a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof. In some embodiments, a composition may comprise an ex-vivo amnion treated with a processing agent, wherein the processed amnion comprises an altered capacity to bind and/or release a pharmaceutical or therapeutic agent. In some embodiments, the processed amnion may comprise an altered capacity to bind and/or release a pharmaceutical or therapeutic agent. In some embodiments, the concentration of the processing agent may be up to 10% weight by volume of the amnion. In some embodiments, the processing agent may comprise an anionic surfactant solution, a strong basic solution, a strong acidic solution, a high concentration salt solution, and/or an oxidizing agent in solution with an alcohol. In some embodiments, the anionic surfactant solution may comprise sodium dodecyl sulfate (SDS), Triton™ X-100, and/or Triton™ X-80.

In some embodiments, the loading capacity of the processed amnion is greater than the loading capacity of the amnion that has not been exposed to the processing agent. In some cases, a loading capacity of the processed amnion is at least 1.2 times greater than the loading capacity of the amnion that has not been exposed to the processing agent. In some cases, a loading capacity of the processed amnion is at least five times greater than the loading capacity of the amnion that has not been exposed to the processing agent.

The loading capacity of a processed amnion may be several times greater than the loading capacity of an unprocessed amnion. In some embodiments, the loading capacity of an unprocessed amnion may be up to about 0.1 mg protein per mg of amnion. In some cases, the capacity of a processed amnion may be up to 3 mg protein per mg of amnion, for example, the capacity may be about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, or about 0.2 mg protein per mg of amnion.

In some embodiments, the loading capacity of a processed amnion may be up to about 5 mg of therapeutic agent per mg of amnion, In some embodiments, the loading capacity of a processed amnion may be several times greater than the loading capacity of an unprocessed amnion. In some cases, the capacity of a processed amnion may be up to 7 mg of therapeutic agent per mg of amnion. In some cases, the capacity of a processed amnion may be up to 10 mg of therapeutic agent per mg of amnion, for example, the capacity may be about 10 mg, about 9.8 mg, about 9.6, about 9.4, about 9.2, about 9, about 8.8, about 8.6, about 8.4, about 8.2, about 8, about 7.8, about 7.6, about 7.4, about 7.2, about 7, about 6.8, about 6.6, about 6.4, about 6.2, about 6, about 5.8, about 5.6, about 5.4, about 5.2, about 5, about 4.8, about 4.6, about 4.4, about 4.2, or about 4 mg, about 3.8, about 3.6, about 3.4, about 3.2, about 3, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, or about 0.1 mg therapeutic agent per mg of amnion.

In some embodiments, the composition comprises about 50% amnion and about 50% processing agent. In some embodiments, the composition comprises up to about 75% processing agent. In other embodiments, the composition comprises at least about 5% processing agent. For example, the composition may comprise about 5%, about 7%, about 10%, about 15%, about 20%, about 25%, about 30%, about 35%, about 40%, about 45%, about 50%, about 55%, about 60%, about 65%, or about 70% processing agent. In some embodiments, the composition comprises at least 25% amnion. In some embodiments, the composition comprises up to about 95% of amnion. For example, the composition may comprise about 30%, about 35%, about 40%, about 45%, about 50%, about 55%, about 60%, about 65%, or about 70% amnion.

In some embodiments, at least one collagen-containing layer of the amnion may be expanded. As used herein, the expansion of a layer may relate to an increase in volume of a given layer of the amnion. In some cases, an epithelial layer of the amnion may be perforated. In certain embodiments, the amnion comprises a therapeutic agent may comprise small molecules, proteins, cytokines, growth factors, and/or cells.

In some embodiments, the amnion may be a sheet. The sheet may be 10 mm to 1 meter in width. In some embodiments, the amnion may be manipulated to reduce the size of amnion particles or pieces. In some embodiments, a size of amnion may be between about 1 μm$^2$ and 10 mm$^2$. In other embodiments, a size of amnion may be between about 10 mm$^2$ and 1000 cm$^2$.

In embodiments, the present invention relates to associated methods of preparing placental tissue products/compositions. In an embodiment, an amnion may be processed with a processing agent to enhance the capacity of the amnion. In some embodiments, the processing agent may sanitize or sterilize the amnion.

In some embodiments, a method for enhancing a loading capacity of an amnion may comprise contacting an amnion with a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof. In certain embodiments, the contact step may comprise submerging, rinsing, perfusing, and/or spraying the amnion. In some cases, the method may further comprise agitating and/or sonicating the amnion. In some cases, the method may further comprise pulverizing, grinding, chopping, or micronizing the amnion. In some examples, the oxidizing agent may comprise hydrogen peroxide and/or peracetic acid.

In some embodiments, the amnion may be processed by submersion, rinsing, spraying, perfusing, or otherwise treating the amnion with a processing agent. In some embodiments, the processing may be performed under static conditions, with agitation, sonication, or otherwise. In some embodiments, the increased capacity of the amnion may permit the amnion to hold an increased amount of therapeutic agent for delivery.

In some embodiments, the composition may further comprise a therapeutic agent. In certain embodiments, the therapeutic agent may comprise any one of small molecules, proteins, cytokines, growth factors, gene therapy agents, cells, and combinations thereof. In some cases, the therapeutic agent may comprise antibiotics. In some cases, the therapeutic agent may comprise analgesics. In some cases, the therapeutic agent may comprise acellular placental products.

In an embodiment, an amnion may be processed with an oxidizing agent to enhance the capacity of the amnion. In some embodiments, a concentration of the oxidizing agent may be up to 10% weight by volume of the processing solution. In some embodiments, the amnion may be processed in a solution comprising hydrogen peroxide. In some embodiments, the hydrogen peroxide concentration may be up to 10% weight by volume of the processing solution. The hydrogen peroxide may sanitize or sterilize the amnion. The hydrogen peroxide may expand the collagen-containing layers of the amnion. This expansion may permit an increased amount of solution to enter the amnion thereby increasing the capacity of the amnion.

In another embodiment, the amnion may be processed in a solution of peracetic acid. In some embodiments, the peracetic acid concentration may be up to 10% weight by volume of the processing solution. The peracetic acid may sanitize or sterilize the amnion. The peracetic acid may perforate or otherwise alter the epithelial layer of the amnion. This alteration may allow an increased amount of solution to enter the amnion, thereby increasing the capacity of the amnion.

In another embodiment, the amnion may be processed in an anionic surfactant solution to expand the capacity of the amnion. Anionic surfactants may include, but are not limited to Triton™ X-100, and/or Triton™ X-80. In some embodiments, the amnion may be processed in ionic detergents, such as sodium dodecyl sulfate. In some embodiments, the amnion may be processed in a basic solution, such as sodium hydroxide, to expand the capacity of the amnion. In some embodiments, the amnion may be processed in an acidic solution, such as acetic acid, to expand the capacity of the amnion.

In other embodiments, the amnion may be processed in a hypertonic solution, for example a solution of greater than 2% sodium chloride, to expand the capacity of the amnion. In other embodiments, the amnion may be processed in a hypotonic solution, for example a solution of less than 0.45% sodium chloride, to expand the capacity of the amnion.

In some embodiments, the amnion may be processed in a solvent to expand the capacity of the amnion. Solvents may include, but are not limited to, alcohols, acetone, and tri (n-butyl) phosphate (TnBP). In some embodiments, the amnion may be processed with Zwitterionic detergents to expand the capacity of the amnion. Zwitterionic detergents include, but are not limited to, 3-((3-cholamidopropyl) dimethylammonio)-1-propanesulfonate) (CHAPS), sulfobetaine-10 (SB-10), and sulfobetaine-16 (SB-16).

In some embodiments, the amnion may be processed in solutions containing a combination of an acid, a base, an anionic detergent, an ionic detergent, a Zwitterionic detergent, an alcohol, an oxidizing agent, hypertonic solution, hypotonic solution, and a solvent. For example, in some embodiments, the amnion may be processed in a solution containing SDS and acetone, TnBP and Triton™ X-100, CHAPS and sodium hydroxide, and peracetic acid in ethanol to expand the capacity of the amnion. In some embodiments, the amnion may be processed with a supercritical fluid.

In another embodiment, the amnion may be processed in a solution of peracetic acid and then processed in a solution of hydrogen peroxide to expand the capacity of the amnion. In some embodiments, the peracetic acid concentration of the initial processing may be up to 10% weight by volume of the processing solution and the hydrogen peroxide concentration of the subsequent processing may be up to 10% weight by volume of the processing solution. In another embodiment, the amnion may be processed in a solution of hydrogen peroxide and then processed in a solution of peracetic acid to expand the capacity of the amnion. In some embodiments, the hydrogen peroxide concentration of the initial processing may be up to 10% weight by volume of the processing solution and the peracetic acid concentration of the subsequent processing may be up to 10% weight by volume of the processing solution.

In some embodiments, an amniotic membrane may be processed to enhance its function as a delivery device for therapeutic agents including small molecules, proteins, cytokines, growth factors, and/or cells. Small molecules may include, but are not limited to: antibiotics, such as penicillins, cephalosporins, cipros, erythromycins; analgesics, such as narcotics, NSAIDs, acetomenophen; vasodilators; vasoconstrictors; neuroleptics; and/or other drugs that may be delivered orally, transdermally or intravenously. Proteins may include, but are not limited to bone morphogenetic protein (BMP-1, BMP-2, BMP-7), insulin-like growth factors (IGF-1), basic fibroblast growth factors (bFGF), nerve growth factors (NGF), and/or vascular endothelial growth factors (VEGF). In some embodiments, therapeutics may include acellular placental products. Gene therapy agents may include nucleic acids, viruses, plasmids, viral vectors, plasmid DNA, linear DNA, mRNA, iRNA, and siRNA. Therapeutic agents that can be used in the described composition can include, for example, those described and set forth in US patent publication number US20060078604 by Kanios, Mantelle, and Nguyen, which is incorporated herein by reference.

In an embodiment, an amnion is loaded with therapeutic agents comprising small molecules, proteins, cytokines, growth factors, cells, and/or gene therapy agents. The processed amnion may be loaded with the therapeutic agent by submersion, rinsing, spraying, or otherwise treating with the protein solution. The loading may be performed under static conditions, with agitation, sonication, or otherwise.

In some embodiments, the loaded amnion may be stored until time of use. In some embodiments, the amnion may be loaded at the time of use. In some embodiments, the loaded amnion may be dehydrated and stored until time of use. In some embodiments, the amnion may be left in sheet form for use. In some embodiments, the processing of the amnion may further comprise pulverizing, grinding, chopping, or micronizing.

In some embodiments, a processed amnion may have improved retention of therapeutic agents, including small molecules, proteins, cytokines, growth factors, cells, acellular placental products, and gene therapy agents. In some embodiments, the processed amnion may have controlled release of therapeutic agents, including small molecules, proteins, cytokines, growth factors, cells, acellular placental products, and gene therapy agents.

To utilize the amnion in enhanced medical applications, in some embodiments, the amnion may be processed in advance of treatment and loaded just prior to patient application. In some embodiments, targeted medical applications to utilize placental tissue to deliver therapeutic agents include but are not limited to wound healing, osteoarthritis, pain management and the like.

In some embodiments, compositions described herein may be used to aid in healing of burns, internal and external ulcers, surgical sites, nerve injuries, or other lesions. In certain embodiments, a composition may be used as a wound covering. In embodiments, the composition may be applied directly to a wound site. In some embodiments, the composition may be in sheet form. In some embodiments, the composition may be applied as an intact sheet. In other embodiments, the composition may be applied as a paste. In other embodiments, the composition may be powder, pulverized particles, or micronized particles.

In some embodiments, compositions may be used for local drug delivery. In some embodiments, compositions may be used for delivery of therapeutic agents including small molecules, proteins, cytokines, growth factors, cells, acellular placental products, and/or gene therapy agents. Small molecules may include, but are not limited to: antibiotics, such as penicillins, cephalosporins, cipros, erythromycins; analgesics, such as narcotics, NSAIDs, acetomenophen; vasodilators; vasoconstrictors; neuroleptics; and/or other drugs that may be delivered orally, transdermally or intravenously. In some embodiments, therapeutics may include acellular placental products. Proteins may include, but are not limited to BMP-1, BMP-2, BMP-7, IGF-1, bFGF, NGF, and/or VEGF. In some embodiments, therapeutics may include gene therapy agents. Gene therapy agents may include, but are not limited to, nucleic acids, viruses, plasmids, viral vectors, plasmid DNA, linear DNA, mRNA, iRNA, and siRNA.

In other embodiments, the composition may be injected. In some embodiments, the therapeutic-loaded processed amnion may be used to control the bacterial growth at a wound site. In some embodiments, the therapeutic-loaded processed amnion may be used to manage pain, e.g., from an injury. In embodiments, the amnion may be loaded with a growth factor and used to help speed healing. In some embodiments, the amnion may be loaded with a bone growth factor, such as BMP-1, 2, or 7, and used to aid in fracture healing. In some embodiments, the amnion may be loaded with a vascular endothelial growth factor (VEGF) and used to aid in healing of damaged blood vessels. In some embodiments, the amnion may be loaded with a nerve growth factor (NGF) to aid in the growth of nerves. In some embodiments, the amnion may be loaded with muscle growth factor, such as IGF-1 or bFGF, to aid in the growth of muscle.

Not intending to be bound by theory, it is believed that a composition with an increased loading capacity and amount of therapeutic retained within the composition may be beneficial for drug delivery.

Also disclosed herein are methods for treating an a condition with an amnion. In some embodiments, a method for treating a condition with an amnion may comprise loading a processed amnion with a therapeutic agent, wherein the therapeutic agent comprises any one of small molecules, proteins, cytokines, growth factors, gene therapy agents, cells, and combinations thereof and placing the loaded amnion at a treatment location. In some embodiments, the processed amnion may release the therapeutic agent at a controlled rate. In certain embodiments, the amnion may be placed by injecting, covering, packing, or enclosing the amnion at the treatment location. In some embodiments, the conditions treated may comprise wound healing, osteoarthritis, and/or pain management.

Embodiments of the present invention, and their advantages are illustrated by the following Examples.

Example 1

An amnion was processed in a solution comprising hydrogen peroxide to expand the capacity of the amnion. The transmission electron microscope (TEM) micrograph of the hydrogen peroxide-processed amnion shows an expansion in the collagen-containing layers, as shown in FIG. 2. This expansion may permit an increased amount of solution to enter the amnion, thereby increasing the capacity of the amnion.

Figure 3:
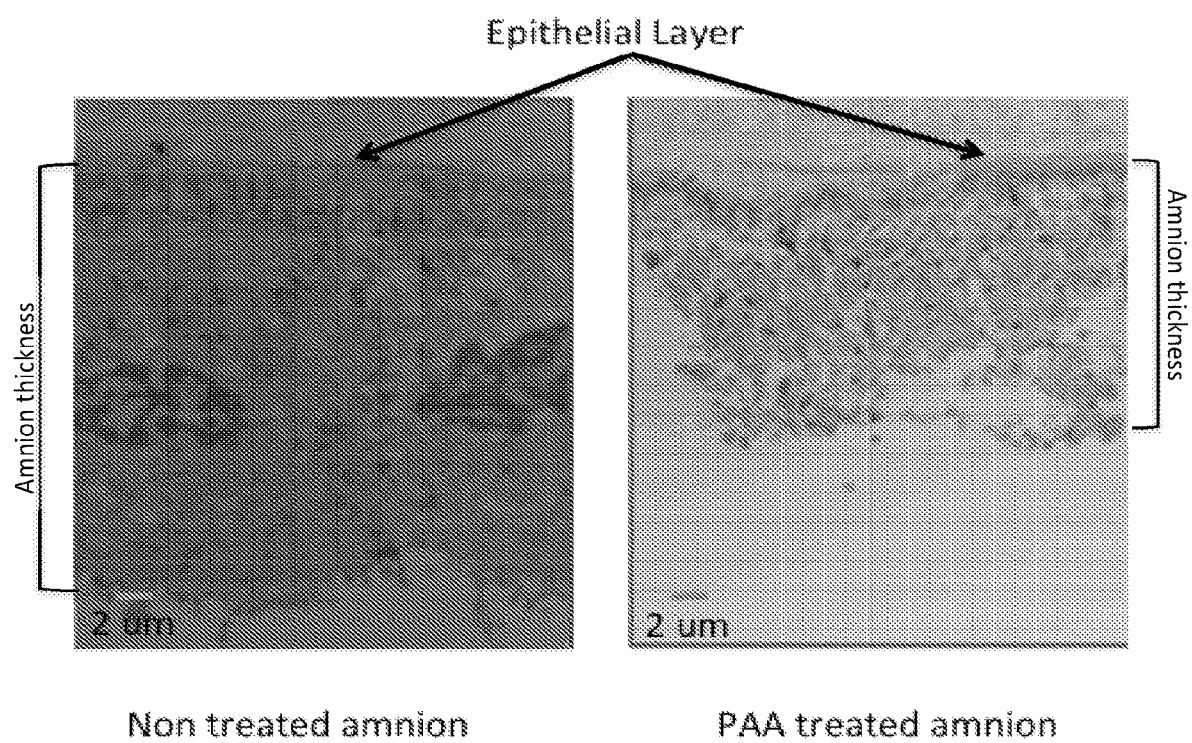
FIG. 3 is a micrograph of an amnion processed in peracetic acid.

An amnion was processed in a solution of peracetic acid to expand the capacity of the amnion. The TEM micrograph of a peracetic acid-processed amnion shows an altered epithelial layer, as shown in FIG. 3. The epithelial layer may be perforated by the processing with peracetic acid, which may allow an increased amount of solution to enter the amnion, thereby increasing the capacity of the amnion.

Example 2

Birth tissue (BT), including placentas and accompanying membranes and umbilical cord, were obtained from an FDA registered human tissue establishment. BT were placed into 0.9% NaCl and kept between 1° C. and 10° C. until arrival at the experimental laboratory. BT arrived within 48 hours of the time of birth. Upon arrival at the laboratory, the amnion was separated from the placental tissue. The amnion was gently cleaned in 0.9% NaCl to remove clots and debris. Solutions of 0.6%, 3%, and 6% hydrogen peroxide ($H_2O_2$) were prepared by diluting a 33% stock solution of hydrogen peroxide with DPBS. Solutions of 0.5%, 1%, and 5% peracetic acid (PAA) were prepared from a 37% stock solution and diluted in DBPS. The non-processed control amnion was stored in DPBS at 4° C. The amnion was divided into equivalent segments. The segments were placed in the respective solutions and stored with gentle agitation for a period of 2 or 24 hours at 4° C. At the end of the processing period, the amnion segments were removed from the solution, rinsed with DPBS and placed on a smooth, non-adhering surface to air dry overnight at ambient conditions. The following day, equal size pieces of the amnion from each solution were divided, weighed, and then placed into DPBS. The amnions were removed at periods of 2 and 24 hours and weighed to determine the amount of DPBS solution loaded into each processed amnion. The resulting data is provided in FIGS. 4 and 5.

Figure 4:
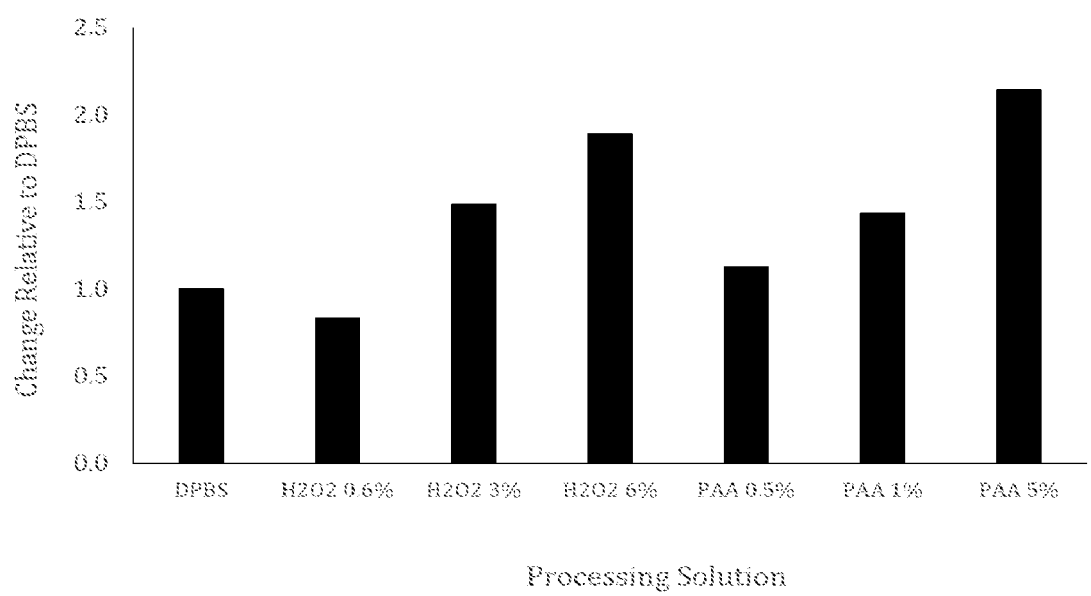
FIG. 4 is a graph showing the loading of processed amnion after a 2-hour soak in Dulbecco's phosphate buffered saline (DPBS).

FIG. 4 shows the loading of Dulbecco's phosphate buffered saline (DPBS) in amnion after processing in various solutions to enhance the capacity of the amnion. DPBS closely approximates the physiological conditions of pH and salinity of the human body. Amnion segments of equivalent size were processed in the expansion solution for a two-hour period (not shown) and a 24-hour period (shown in FIG. 4) and then soaked in a solution of DPBS for 2 hours and then weighed.

The data is presented as compared to data from a non-processed amnion control that was maintained in DPBS. The segments of amnion processed for 2 hours showed no improvement in loading capacity as compared to the non-processed DPBS control segment. However, segments of amnion processed with the agent for 24 hours showed improved loading capacity. In particular, amnion treated with peracetic acid showed the largest increase in capacity, especially at the highest concentrations (shown in FIG. 4). The 5% peracetic acid processed amnion more than doubled the amount loaded in the amnion as compared to the control DPBS. The hydrogen peroxide-treated amnion exhibited similar behavior, with the 3% and 6% hydrogen peroxide solution processed amnions exhibiting an increased loading as compared to the control. The Change Relative to DPBS is measured as [weight change of a sample]/[weight change of control], where weight change is [final weight-starting weight].

Figure 5:
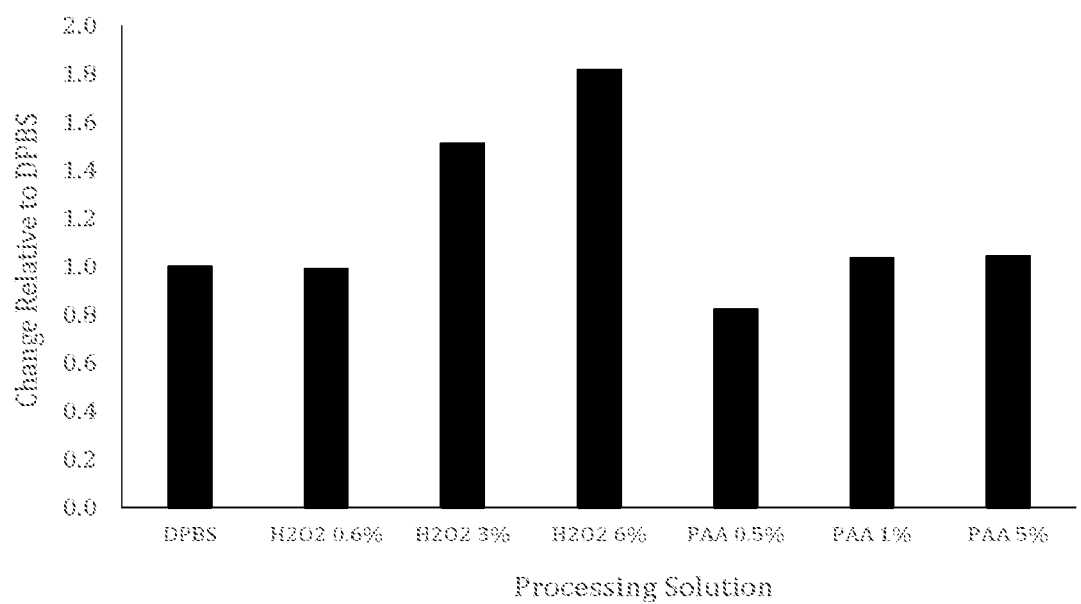
FIG. 5 is a graph showing the loading of processed amnion after a 24-hour soak in DPBS.

FIG. 5 shows the loading of DPBS in amnion after processing in various solutions to enhance the capacity of the amnion. Amnion segments of equivalent size were processed in the expansion solution for a two-hour period (not shown) and a 24-hour period (shown in FIG. 5) and then soaked in a solution of DPBS for 24 hours and then weighed. The data is presented relative to a non-processed amnion control that was maintained in DPBS. The segments of amnion processed for 2 hours showed no improvement in loading capacity as compared to the non-processed DPBS control segment. However, most of the segments of amnion processed with the agent demonstrated a loading capacity at least equivalent to DPBS, with several greatly exceeding the capacity of the control DPBS. In particular, hydrogen peroxide at 3% and 6% showed the largest increase in capacity (shown in FIG. 5). The 3% hydrogen peroxide demonstrated a 51% increase while the 6% hydrogen peroxide solution processed amnions demonstrated an 81% increase in the level of DPBS loaded as compared to the control. The 1% and 5% peracetic acid-processed amnion demonstrated a 3% and 4% increase respectively in loading capacity as compared to the control DPBS. Not to be bound by theory, the non-processed control may have demonstrated increased loading due to the longer soak time (24 hours as compared to 2 hours). The processed amnion also loaded an increased amount of DPBS, but the increase was similar to the non-processed amnion.

Example 3

Birth tissue (BT), including placentas and accompanying membranes and umbilical cord, were obtained from an FDA registered human tissue establishment. BT were placed into 0.9% NaCl and kept between 1° C. and 10° C. until arrival at the experimental laboratory. BT arrived within 48 hours of the time of birth. Upon arrival at the laboratory, the amnion was separated from the placental tissue. The amnion was gently cleaned in 0.9% NaCl to remove clots and debris. Solutions of 0.6%, 3%, and 6% $H_2O_2$ were prepared by diluting a 33% stock solution of $H_2O_2$ with DPBS. Solutions of 0.5%, 1%, and 5% PAA were prepared from a 37% stock solution and diluted in DBPS. The non-processed control amnion was stored in DPBS at 4° C. The amnion was divided into equivalent segments. One group of amnion was processed in DBPS, 0.6% $H_2O_2$, or 1% PAA for 24 hours. Another group of amnion was processed with 1% PAA for 22 hours and then processed with 0.6% $H_2O_2$ for 2 hours. A final group was processed with 0.6% $H_2O_2$ for 2 hours followed by 1% PAA for 22 hours. All amnions were processed at 4° C. for a total of 24 hours. At the end of the processing period, the amnion segments were removed from the solution, rinsed with DPBS and placed on a smooth, non-adhering surface to air-dry overnight at ambient conditions. The following day, equal size pieces of the amnion from each solution were divided, weighed, and then placed into a solution containing 7.5 mg/mL protein and allowed to soak for 2 hours. The amnions were removed and the total protein loaded into the amnion was quantified using a Bradford Assay. The amount of protein loaded on the amnion was determined by the difference between the concentration of the starting protein solution (7.5 mg/mL) and the resulting concentration of the solution exposed to the amnion. The resulting data from is provided in FIG. 6.

Figure 6:
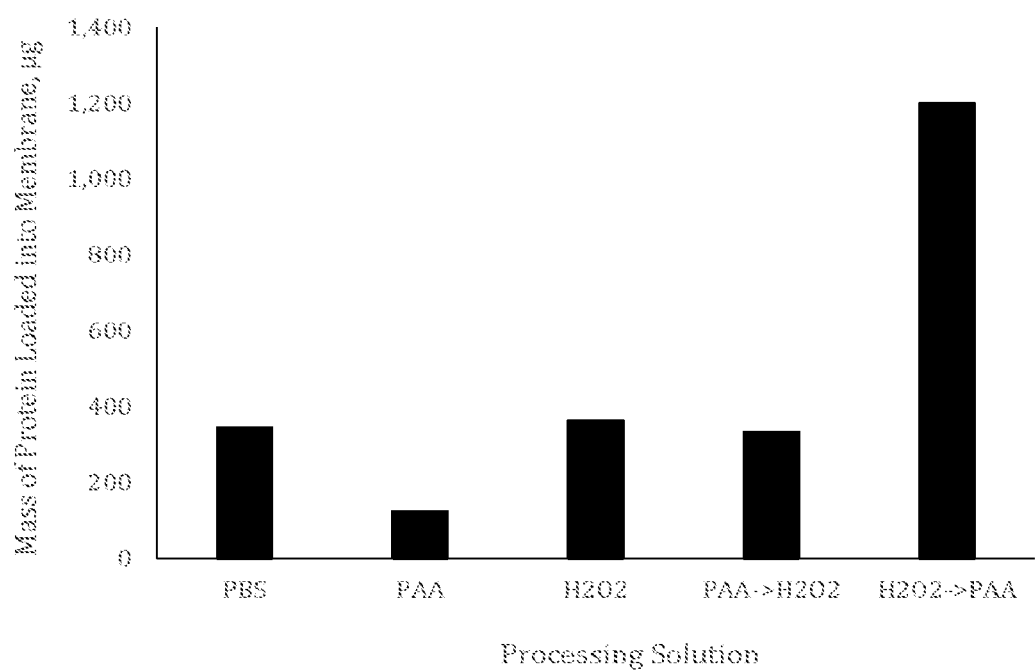
FIG. 6 is a graph showing the loading of protein in processed amnion.

FIG. 6 shows the loading of proteins in amnion after processing in various solutions to enhance the capacity of the amnion. Amnion segments of equivalent size were processed in the expansion solution for a 24-hour period and then soaked in a protein solution for two hours followed by measurement of the loaded protein concentration. For two segments, processing solutions were used sequentially, with the fourth segment processed first in the hydrogen peroxide solution for 2 hours and then processed in the peracetic acid solution for 22 hours. The fifth amnion segment, processed first in hydrogen peroxide for 2 hours and then processed in peracetic acid for 22 hours, showed a significant increase in protein loading capacity as compared to the non-processed DPBS control segment, at a nearly quadruple the loading. As shown in FIG. 6, the amount of protein loaded in the processed amnion was generally equivalent to or greater than the control. Only the exclusive peracetic acid processed amnion demonstrated a lower loading level compared to the control. Surprisingly, the amnion processed with hydrogen peroxide followed by peracetic acid demonstrated a significant increase in the loading level as compared to the control.

Example 4

Birth tissue (BT), including placentas and accompanying membranes and umbilical cord, were obtained from an FDA registered human tissue establishment. BT were placed into 0.9% NaCl and kept between 1° C. and 10° C. until arrival at the experimental laboratory. BT arrived within 48 hours of the time of birth. Upon arrival at the laboratory, the amnion was separated from the placental tissue. The amnion was gently cleaned in 0.9% NaCl to remove clots and debris. Solutions of 0.6%, 3%, and 6% $H_2O_2$ were prepared by diluting a 33% stock solution of $H_2O_2$ with DPBS. Solutions of 0.5%, 1%, and 5% PAA were prepared from a 37% stock solution and diluted in DBPS. The non-processed control amnion was stored in DPBS at 4° C. The amnion was divided into equivalent segments. One group of amnion was processed in DBPS, 0.6% $H_2O_2$, or 1% PAA for 24 hours. Another group of amnion was processed with 1% PAA for 22 hours and then processed with 0.6% $H_2O_2$ for 2 hours. A final group was processed with 0.6% $H_2O_2$ for 2 hours followed by 1% PAA for 22 hours. All amnions were processed at 4° C. for a total of 24 hours. At the end of the processing period, the amnion segments were removed from the solution, rinsed with DPBS and placed on a smooth, non-adhering surface to air-dry overnight at ambient conditions. The following day, equal size pieces of the amnion from each solution were divided, weighed, and then placed into a solution containing 7.5 mg/mL protein and allowed to soak for 2 hours. The amnions were removed and the release assay was started. The amnions were covered with 200 μL DPBS. At 6, 12, and 24 hours and 2, 3, 4, and 5 days, the DPBS solution was removed and the DPBS solution was frozen until the end of the experiment. Fresh DPBS solution was placed on the amnion at each sample point. A Bradford Assay was used to quantify the protein released for each sample. The cumulative percent released is the [sum of the mass released up to and including the time point of interest]/[initial loaded mass]. For example, the cumulative percent released at time point 2 for a 6 unit starting mass sample may be [2 units on time point 1+1 units on time point 2]/[6 unit], which gives a 50% cumulative release at time point 2. The resulting data from is provided in FIG. 7.

Figure 7:
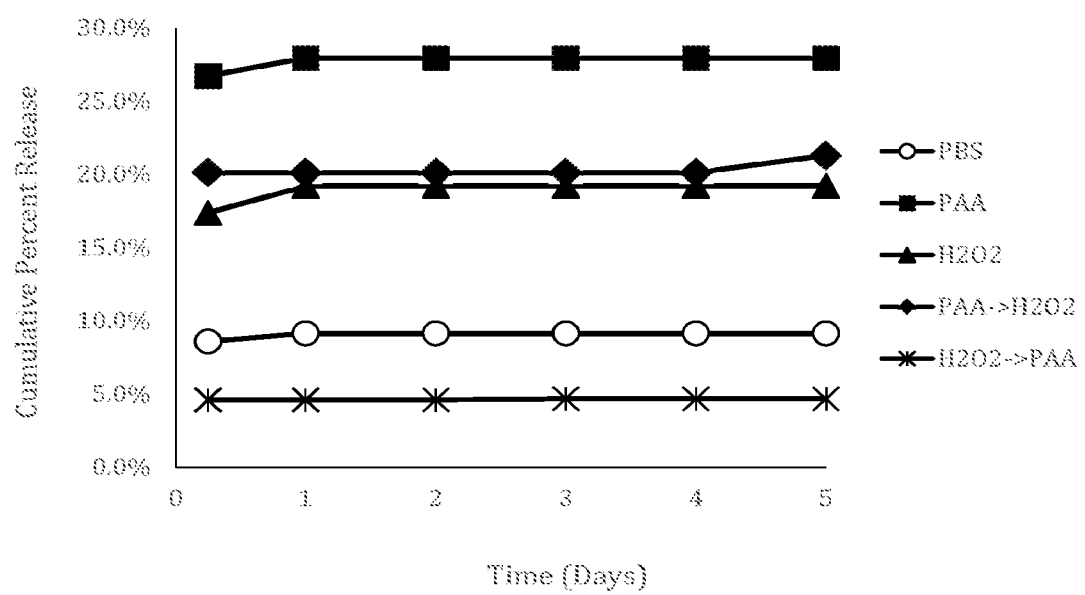
FIG. 7 is a graph showing the cumulative percent release of protein from the processed and loaded amnion of FIG. 7.

FIG. 7 shows the cumulative release of proteins from amnion loaded with protein after processing in various solutions to enhance the capacity of the amnion. Amnion segments of equivalent size were processed in the expansion solution for a 24-hour period and then soaked in a protein solution for two hours followed by measurement of the loaded protein concentration of the amnion. To determine the amount of protein released, the loaded amnion was placed in a solution of DPBS and the amount of released proteins was measured. As with the protein loading method, the processing solutions were combined for two segments, with the segment processed in the peroxide solution for 2 hours and processed in the peracetic acid solution for 22 hours. All process treatments showed fairly strong retention of protein over the time period observed, yielding not more than 30% cumulative percent release. Processing the amnion with hydrogen peroxide and then peracetic acid yielded the best retention of 4.7%, performing nearly twice as well as the DPBS control at 9.1%. The amnion processed with hydrogen peroxide and then peracetic acid retained 95% of the protein loaded in the processed amnion. Not to be bound by theory, the retention of the protein within the amnion coupled with the perforated epithelial layer and expanded collagen layers, as shown in FIGS. 2 and 3, may provide a means to deliver a therapeutic agent to the target region for an extended period of time. A loaded amnion that retains a therapeutic agent within the amnion and demonstrates a low release rate may provide improved delivery of the therapeutic agent in a medical application.

Example 5

Birth tissue (BT), including placentas and accompanying membranes and umbilical cord, were obtained from an FDA registered human tissue establishment. BT were placed into 0.9% NaCl and kept between 1° C. and 10° C. until arrival at the experimental laboratory. BT arrived within 48 hours of the time of birth. Upon arrival at the laboratory, the amnion was separated from the placental tissue. The amnion was gently cleaned in 0.9% NaCl to remove clots and debris. Solutions of 0.6%, 3%, and 6% $H_2O_2$ were prepared by diluting a 33% stock solution of $H_2O_2$ with DPBS. Solutions of 0.5%, 1%, and 5% PAA were prepared from a 37% stock solution and diluted in DBPS. The non-processed control amnion was stored in DPBS at 4° C. The amnion was divided into equivalent segments. The segments were placed in the respective solutions and stored with gentle mixing for a period of 24 hours at 4° C. At the end of the processing period, the amnion segments were removed from the solution, rinsed with DPBS and placed on a smooth, non-adhering surface to air-dry overnight at ambient conditions. The following day, equal size pieces of the amnion from each solution were divided, weighed, and then placed into 100 μL of 20 mg/mL ciprofloxacin (or 2 mg per amnion segment). The amnion were permitted to soak in the ciprofloxacin solution for 2 hours and then 1 mL of DPBS was added to the tube containing the tissue and ciprofloxacin solution to start the release portion of the assay. At 6, 12, and 24 hours and 2, 3, 4, and 5 days, 200 μL of the solution on each amnion segment was removed and the DPBS solution was frozen until the completion of the experiment and 200 μL of fresh DPBS was added back in the solution on each amnion segment. A Bradford Assay was used to quantify the protein released for each sample. The cumulative ciprofloxacin released was quantified for each processing solution sample by measuring the absorbance at 280 nM in a microplate reader. The resulting data is provided in FIG. 8.

Figure 8:
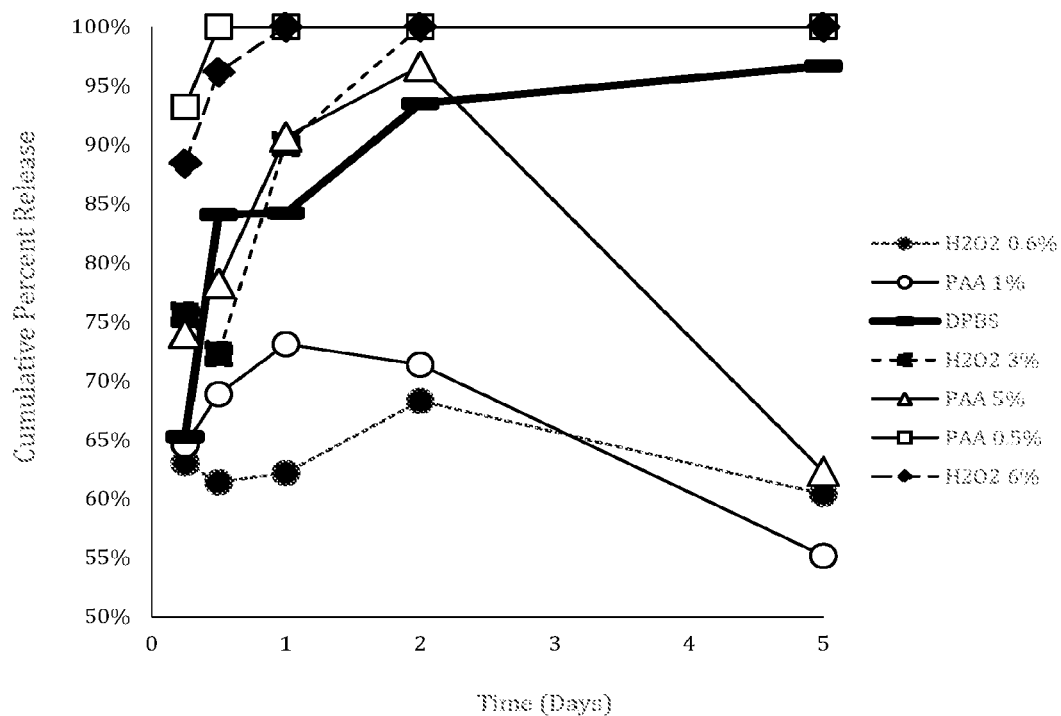
FIG. 8 is a graph showing the cumulative percent release of ciprofloxacin with flux from processed amnion.

FIG. 8 shows the cumulative release of ciprofloxacin from amnion loaded with ciprofloxacin after processing in various solutions to enhance the capacity of the amnion. Ciprofloxacin is a small molecule anti-bacterial agent. Amnion segments of equivalent size were processed in the expansion solution for a 24-hour period and then soaked in a ciprofloxacin solution of known concentration for two hours. To determine the amount of ciprofloxacin released, the loaded amnion was placed in a solution of DPBS and the amount of released ciprofloxacin was measured, while allowing for flux. All amnion segments processed with peracetic acid performed better than the DPBS control and demonstrated a lower cumulative percent of ciprofloxacin released. The amnion processed with the lowest concentration of hydrogen peroxide demonstrated the greatest level of improvement over the DPBS control segment with as much as 30% of the ciprofloxacin retained in the processed amnion. The DPBS control has a burst release of 85% of the ciprofloxacin within the first 12 hours, but then slowed and ended with 97% of the ciprofloxacin released. At two days, two treatments (0.6% peroxide and 1% peracetic acid) had yet to reach the 85% ciprofloxacin release that the control group showed in the first 12 hours. This low release level may be desirable for drug delivery. Processing the amnion with 0.6% hydrogen peroxide, 1% peracetic acid, or 5% peracetic acid all retained the ciprofloxacin for a longer period than the DPBS control.

Illustrations of Suitable Alloys, Products, and Methods

As used below, any reference to a series of illustrative composition or methods is to be understood as a reference to each of those compositions or methods disjunctively (e.g., "Illustrations 1-4" is to be understood as "Illustration 1, 2, 3, or 4").

Illustration 1 is a composition comprising an amnion treated with a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof.

Illustration 2 is the composition of any preceding or subsequent illustration, wherein the processed amnion comprises an altered capacity to bind and/or release a pharmaceutical or therapeutic agent.

Illustration 3 is the composition of any preceding or subsequent illustration, wherein the oxidizing agent comprises any one of hydrogen peroxide and peracetic acid.

Illustration 4 is the composition of any preceding or subsequent illustration, wherein a concentration of the processing agent may be up to 10% weight by volume of the amnion.

Illustration 5 is the composition of any preceding or subsequent illustration, wherein a loading capacity of the processed amnion is at least 1.2 times greater than the loading capacity of the amnion that has not been exposed to the processing agent.

Illustration 6 is the composition of any preceding or subsequent illustration, wherein at least one collagen-containing layer of the amnion is expanded.

Illustration 7 is the composition of any preceding or subsequent illustration, wherein an epithelial layer of the amnion is perforated.

Illustration 8 is the composition of any preceding or subsequent illustration, wherein the amnion comprises a therapeutic agent comprising small molecules, proteins, cytokines, growth factors, and/or cells.

Illustration 9 is the composition of any preceding or subsequent illustration, wherein the amnion is a sheet.

Illustration 10 is the composition of any preceding or subsequent illustration, wherein a size of amnion is between about 1 $\mu m^2$ and 10 $mm^2$.

Illustration 11 is the composition of any preceding or subsequent illustration, wherein a size of amnion is between about 10 $mm^2$ and 1000 $cm^2$.

Illustration 12 is the composition of any preceding or subsequent illustration, further comprising a therapeutic agent.

Illustration 13 is the composition of any preceding or subsequent illustration, wherein the therapeutic agent comprises any one of small molecules, proteins, cytokines, growth factors, gene therapy agents, cells, and combinations thereof.

Illustration 14 is the composition of any preceding or subsequent illustration, wherein the therapeutic agent comprises antibiotics.

Illustration 15 is the composition of any preceding or subsequent illustration, wherein the therapeutic agent comprises analgesics.

Illustration 16 is the composition of any preceding or subsequent illustration, wherein the therapeutic agent comprises acellular placental products.

Illustration 17 is a method for enhancing a loading capacity of an amnion comprising contacting an amnion with a processing agent, wherein the processing agent comprises any one of an acid, a base, an anionic detergent, an ionic detergent, a Zwitterionic detergent, an alcohol, an oxidizing agent, hypertonic solution, hypotonic solution, a solvent, a supercritical fluid, and combinations thereof.

Illustration 18 is the method of any preceding or subsequent illustration, wherein the contact step comprises submerging, rinsing, perfusing, and/or spraying the amnion.

Illustration 19 is the method of any preceding or subsequent illustration, wherein the oxidizing agent comprises hydrogen peroxide and/or peracetic acid.

Illustration 20 is the method of any preceding or subsequent illustration, wherein a concentration of the oxidizing agent is up to 10% weight by volume of the amnion.

Illustration 21 is the method of any preceding or subsequent illustration, further comprising agitating and/or sonicating the amnion.

Illustration 22 is the method of any preceding or subsequent illustration, further comprising pulverizing, grinding, chopping, or micronizing the amnion.

Illustration 23 is a method for treating a condition with an amnion comprising: loading a processed amnion with a therapeutic agent, wherein the therapeutic agent comprises any one of small molecules, proteins, cytokines, growth factors, gene therapy agents, cells, and combinations thereof and placing the loaded amnion at a treatment location of a patient.

Illustration 24 is the method of any preceding or subsequent illustration, wherein the processed amnion releases the therapeutic agent at a controlled rate.

Illustration 25 is the method of any preceding or subsequent illustration, wherein the placing comprises injecting, covering, packing, or enclosing the amnion at the treatment location.

Illustration 26 is the method of any preceding or subsequent illustration, wherein the conditions treated comprise wound healing, osteoarthritis, and/or pain management.

Various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

While the invention is susceptible to various modifications and alternative constructions, certain illustrated embodiments thereof are shown in the drawings and described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The terms "comprising," "having," "including," and "containing" are to be construed as open-ended terms (i.e., meaning "including, but not limited to") unless otherwise noted. The term connected is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individual recited herein. All methods described herein can be performed in any suitable order unless otherwise indicated or clearly contradicted by context. The use of any and all examples or exemplary language is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated or otherwise clearly contradicted by context.

What is claimed:

1. A method of preparing a composition for treatment of a wound or lesion in a subject in need thereof, comprising:
    (a) contacting an ex-vivo amnion comprising a collagen-containing layer with an amount of a processing agent effective for expanding the collagen-containing layer; and
    (b) expanding the collagen-containing layer of the ex-vivo amnion, wherein the expanded collagen-containing layer increases a capacity of the ex-vivo amnion to receive a therapeutic agent for treatment of the wound or lesion in the subject.

2. The method of claim 1, wherein the therapeutic agent comprises acellular placental products.

3. The method of claim 1, wherein contacting the ex-vivo amnion comprises submerging the ex-vivo amnion in a solution of the processing agent.

4. The method of claim 1, wherein the processing agent comprises an oxidizing agent.

5. The method of claim 1, wherein the amnion comprises at least one epithelial layer.

6. The method of claim 1, wherein the composition is for wound healing.

7. A method of preparing a composition for treatment of a wound or lesion in a subject in need thereof, comprising:
    (a) contacting an ex-vivo amnion comprising a collagen-containing layer with an amount of a processing agent effective for expanding the collagen-containing layer; and
    (b) expanding the collagen-containing layer of the ex-vivo amnion; and
    (c) loading the expanded ex-vivo amnion with a therapeutic agent, wherein the expanded collagen-containing layer has an increased capacity for holding the therapeutic agent.

8. The method of claim 7, wherein the therapeutic agent comprises acellular placental products.

9. The method of claim 7, wherein contacting the ex-vivo amnion comprises submerging the ex-vivo amnion in a solution of the processing agent.

10. The method of claim 7, wherein the processing agent comprises an oxidizing agent.

11. The method of claim 7, wherein the amnion comprises at least one epithelial layer.

12. The method of claim 7, wherein the composition is for wound healing.

13. The method of claim 7, wherein loading of the ex-vivo amnion comprises submerging the ex-vivo amnion in a solution of the therapeutic agent.

14. The method of claim 7, wherein loading of the ex-vivo amnion comprises agitation.

* * * * *